United States Patent
Kawaguchi et al.

(10) Patent No.: US 11,399,778 B2
(45) Date of Patent: Aug. 2, 2022

(54) MEASURING INSTRUMENT ATTACHMENT ASSIST DEVICE AND MEASURING INSTRUMENT ATTACHMENT ASSIST METHOD

(71) Applicant: NATIONAL INSTITUTE OF ADVANCED INDUSTRIAL SCIENCE AND TECHNOLOGY, Tokyo (JP)

(72) Inventors: Hiroshi Kawaguchi, Tsukuba (JP); Toru Yamada, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 57 days.

(21) Appl. No.: 16/500,664

(22) PCT Filed: Apr. 2, 2018

(86) PCT No.: PCT/JP2018/014158
§ 371 (c)(1),
(2) Date: Oct. 3, 2019

(87) PCT Pub. No.: WO2018/186363
PCT Pub. Date: Oct. 11, 2018

(65) Prior Publication Data
US 2020/0196963 A1 Jun. 25, 2020

(30) Foreign Application Priority Data

Apr. 7, 2017 (JP) .............................. JP2017-076815
Sep. 26, 2017 (JP) .............................. JP2017-184998

(51) Int. Cl.
*A61B 5/00* (2006.01)
*G06T 19/00* (2011.01)
(Continued)

(52) U.S. Cl.
CPC ............ *A61B 5/744* (2013.01); *A61B 5/0042* (2013.01); *G01B 11/24* (2013.01); *G06T 7/344* (2017.01);
(Continued)

(58) Field of Classification Search
CPC .................. A61B 5/0042; G06T 19/00; G06T 2207/30016; G06T 2210/41
See application file for complete search history.

(56) References Cited

U.S. PATENT DOCUMENTS

2010/0295983 A1* 11/2010 Nozawa ........... H04N 5/225251
                                                     348/333.01
2014/0267662 A1*  9/2014 Lampo ................... G16H 50/70
                                                          348/77
2016/0042557 A1*  2/2016 Lin ........................... G06T 7/73
                                                          345/426

FOREIGN PATENT DOCUMENTS

JP        2003088528 A     3/2003
JP        2006320425 A    11/2006
(Continued)

OTHER PUBLICATIONS

Aasted et al. (Anatomical guidance for functional near-infrared spectroscopy: Atlas Viewer tutorial, Neurophotonics, 2015) (Year: 2015).*

(Continued)

*Primary Examiner* — Kyle Zhai
(74) *Attorney, Agent, or Firm* — Muncy, Geissler, Olds & Lowe, P.C.

(57) ABSTRACT

A measuring instrument attachment assist device which includes: a coordinate detector which detects coordinates of predetermined feature points from an image obtained by capturing an image of a subject; a conversion parameter calculator which calculates a projection conversion parameter for converting the coordinates of the feature points in a (Continued)

model image into the coordinates obtained by the detection; a designating unit which designates a position of a measuring instrument attached to the subject in the model image; a coordinate converter which converts a coordinate of the position designated by using the designating unit, by using the projection conversion parameter; and a display which displays the coordinate obtained by the conversion by the coordinate converter, on the image obtained by the capturing.

8 Claims, 9 Drawing Sheets

(51) Int. Cl.
    *G06T 7/33*           (2017.01)
    *G01B 11/24*         (2006.01)
    *G06T 15/08*         (2011.01)

(52) U.S. Cl.
    CPC .............. *G06T 15/08* (2013.01); *G06T 19/00* (2013.01); *G06T 2207/30016* (2013.01); *G06T 2210/41* (2013.01)

(56) References Cited

FOREIGN PATENT DOCUMENTS

| | | |
|---|---|---|
| JP | 2009261588 A | 11/2009 |
| JP | 2010502343 A | 1/2010 |
| JP | 2014030621 A | 2/2014 |
| JP | 2015077331 A | 4/2015 |
| JP | 2017038878 A | 2/2017 |
| WO | WO2014184904 A1 | 11/2014 |

OTHER PUBLICATIONS

Office Action dated Dec. 8, 2020 in JP Application No. 2019-511239 (8 pages).

Office Action dated Sep. 7, 2021 in CN Application No. 20188002306. 4.X, 23 pages, w/English-translation.

Aasted et al., "Anatomical guidance for functional near-infrared spectroscopy: AtlasViewer tutorial, Neurophotonics", Dec. 31, 2015, pp. 020801 (1-16).

\* cited by examiner

MEASURING INSTRUMENT ATTACHMENT ASSIST DEVICE AND MEASURING INSTRUMENT ATTACHMENT ASSIST METHOD

TECHNICAL FIELD

The present invention relates to a device and a method which assist attachment of a measuring instrument which obtains biological information to a subject.

BACKGROUND ART

Functional near infrared spectroscopy (fNIRS) is known as a method for observing an intra-brain activity by non-invasive means. This fNIRS needs to place a probe in contact with a direct upper side of a desired brain region which is an observation target. Hence, as disclosed in patent documents 1 and 2, there are devised assist systems which assist a subject to attach a holder including a probe to a head.

CITATION LIST

Patent Document

[patent document 1] JP 2009-261588 A
[patent document 2] JP 2015-77331 A

SUMMARY OF INVENTION

Problem to be Solved by the Invention

A technique disclosed in patent document 1 needs to fix the head of the subject to a magnetic field source per measurement, record feature points by an electromagnetic sensor, and then attach the probe, and therefore has a problem that restriction with respect to the subject is high, and a preparation operation before measurement is also complicated.

Furthermore, a technique disclosed in patent document 2 needs to attach an optical marker to the subject per measurement, and accordingly needs a brace which stably fixes the optical marker irrespectively of the shape of the head. Such a brace needs to be designed so as not to influence the probe or a fixture which fixes the probe, and trial and error are required. Furthermore, this technique only improves reproducibility of a position of the optical marker, and does not yet solve a task regarding how to perform positioning when measurement is performed for the first time.

The present invention has been made to solve such a problem, and an object of the present invention is to provide a device and a method which assist easy and accurate attachment of a measuring instrument such as a probe at a designated position of a subject.

Means to Solve the Problem

To solve the above task, the present invention provides a measuring instrument attachment assist device which includes: a coordinate detector structured to detect a coordinate of a predetermined feature point from an image obtained by capturing an image of a subject; a conversion parameter calculator structured to calculate a projection conversion parameter for converting a coordinate of the feature point in a model image into the coordinate obtained by the detection; a designating unit structured to designate a position of a measuring instrument attached to the subject in the model image; a coordinate converter structured to convert a coordinate of the position by using the projection conversion parameter, the position being designated by using the designating unit; and a display structured to display the coordinate obtained by the conversion by the coordinate converter, on the image obtained by the capturing.

Furthermore, to solve the above task, the present invention provides a measuring instrument attachment assist device which includes: a coordinate detector structured to detect a coordinate of a predetermined feature point from an image obtained by capturing an image of an external appearance of a subject; a conversion parameter calculator structured to calculate a projection conversion parameter for converting a coordinate of the feature point in a brain surface shape image of the subject into the coordinate obtained by the detection; and an image synthesizer structured to synthesize the brain surface shape image and the image obtained by the capturing by finding corresponding points of the image obtained by the capturing and the brain surface shape image by using the projection conversion parameter, and overlaying the corresponding points.

Furthermore, to solve the above task, the present invention provides a measuring instrument attachment assist method which includes: a first step of detecting a coordinate of a predetermined feature point from an image obtained by capturing an image of a subject; a second step of calculating a projection conversion parameter for converting a coordinate of the feature point in a model image into the coordinate obtained by the detection; and a third step of converting a position coordinate by using the projection conversion parameter, and displaying the converted coordinate in the image obtained by the capturing, the position coordinate being a position coordinate which is designated in the model image, and at which the measuring instrument is attached to the subject.

Effects of Invention

According to the present invention, it is possible to easily and accurately attach a measuring instrument such as a probe to a designated position on a subject.

MODE FOR CARRYING OUT THE INVENTION

Figure 1:
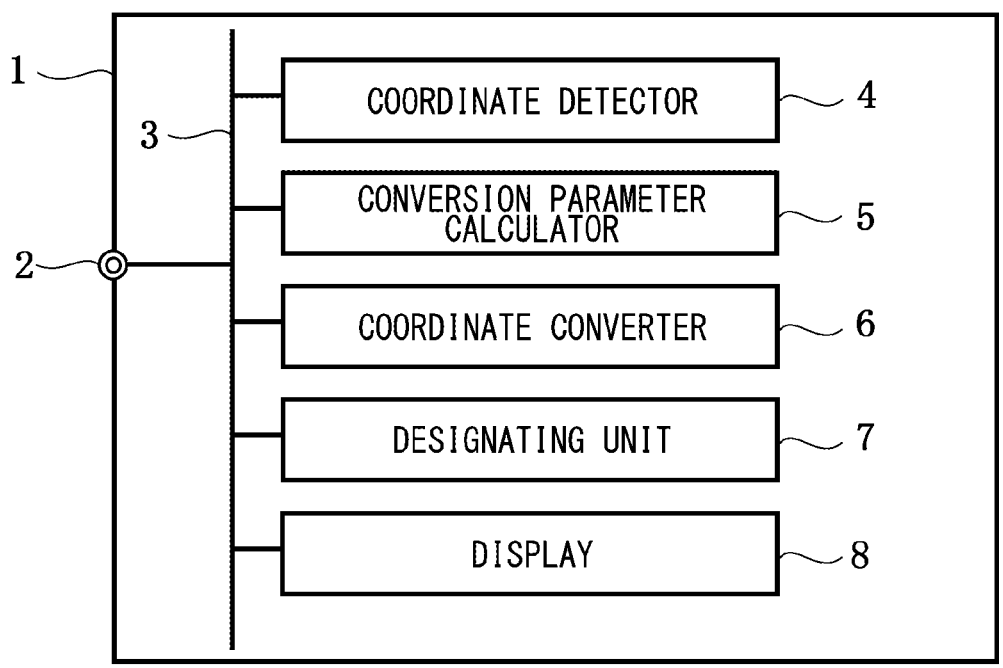
FIG. 1 is a block diagram illustrating a configuration example of a measuring instrument attachment assist device according to a first embodiment of the present invention.

Hereinafter, embodiments of the present invention will be described in detail with reference to drawings. In this regard, the same reference numerals in the drawings indicate the same or corresponding components.

First Embodiment

A measuring instrument attachment assist device according to the first embodiment of the present invention uses feature points of a shape of a subject head as reference markers without using a special marker. That is, the above feature points are automatically detected from an image obtained by capturing an image of the head of the subject. Furthermore, this function is executed targeting at a moving video image, and the reference markers are detected in a real time. Subsequently, this measuring instrument attachment assist device finds a projection conversion parameter which makes a reference point of a model image match with the reference markers detected by capturing the image of the head of the subject, and an attachment position of a measuring instrument set on a model image is projected on the above moving video image by using the found parameter. Thus, the measuring instrument attachment assist device realizes a real time indication on a moving image at a position to which the measuring instrument needs to be attached to assist the subject to attach the measuring instrument to a correct position. Hereinafter, this measuring instrument attachment assist device will be more specifically described.

FIG. 1 is a block diagram illustrating a configuration example of the measuring instrument attachment assist device according to the first embodiment of the present invention. As illustrated in FIG. 1, the measuring instrument attachment assist device 1 according to the first embodiment of the present invention includes an input terminal 2, a bus 3 which is connected to the input terminal 2, and a coordinate detector 4, a conversion parameter calculator 5, a coordinate converter 6, a designating unit 7 and a display 8 which are respectively connected to the bus 3.

Figure 2:
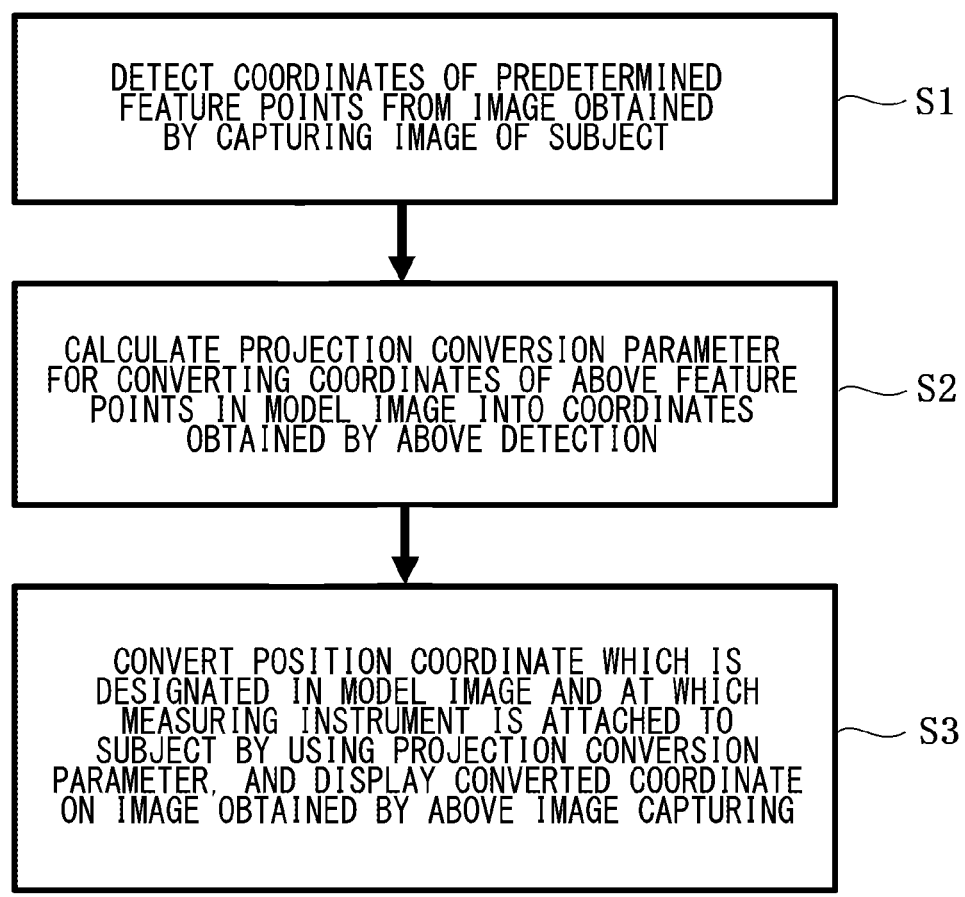
FIG. 2 is a flowchart illustrating a measuring instrument attachment assist method according to an embodiment of the present invention.

FIG. 2 is a flowchart illustrating the measuring instrument attachment assist method according to the embodiment of the present invention. A case where this method is realized by using the measuring instrument attachment assist device 1 illustrated in FIG. 1 will be described below. However, this method may be executed by using other means, and is naturally not limited to a case where the measuring instrument attachment assist device 1 is used.

First, in step S1, the coordinate detector 4 detects coordinates of predetermined feature points from an image obtained by capturing an image of a subject such as a patient. Next, in step S2, the conversion parameter calculator 5 calculates a projection conversion parameter for converting the coordinates of the feature points in a model image into the coordinates obtained by the detection. Next, in step S3, the coordinate converter 6 converts a position coordinate which is designated in the model image by a user by using the designating unit 7, and at which the measuring instrument is attached to the subject, by using the projection conversion parameter, and the display 8 displays the converted coordinate on the image obtained by the capturing.

Figure 3:
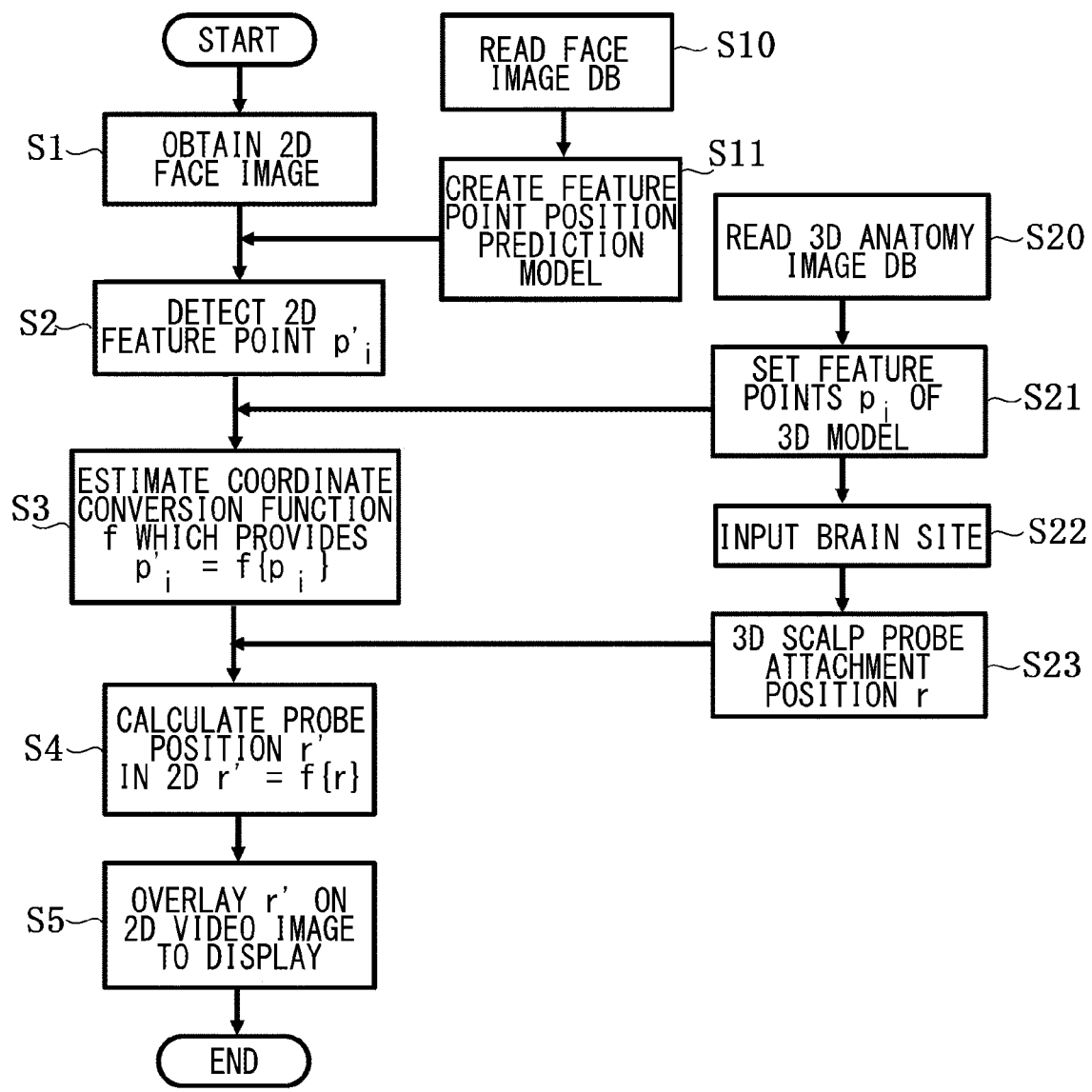
FIG. 3 is a flowchart illustrating a specific example of the measuring instrument attachment assist method illustrated in FIG. 2.

FIG. 3 is a flowchart illustrating a specific example of a measuring instrument attachment assist method illustrated in FIG. 2. An outline of this specific example will be described below with reference to FIG. 3.

A face image database (face image DB) and a three-dimensional anatomy image database (3D anatomy image DB) are prepared in advance. Furthermore, a face image is read from the face image DB in step S10 as pre-processing, and a feature point position prediction model is created in step S11.

The measuring instrument attachment assist device 1 obtains a two-dimensional face image from an outside via the input/output terminal 2 in step S1. In addition, although not illustrated, the measuring instrument attachment assist device 1 may further include an imager, and store in an unillustrated storage the two-dimensional face image captured by the imager.

Next, in step S2, the coordinate detector 4 detects a feature point $p'_i$ from the two-dimensional face image obtained in step S1 by using a prediction model created in step S11.

On the other hand, when a three-dimensional model is read from the 3D anatomy image DB in step S20 and a feature point $p_i$ of the three-dimensional model is set by the user in step S21 as pre-processing, the conversion parameter calculator 5 estimates a coordinate conversion function f which converts the feature point $p_i$ into the feature point $p'_i$.

Furthermore, when the user further designates a site of a brain which needs to be measured on the three-dimensional model by using the designating unit 7, a probe attachment position r with respect to a scalp in the three-dimensional model is determined in step S23.

Thus, in step S4, the coordinate converter 6 calculates a probe attachment position r' on the two-dimensional image corresponding to the probe attachment position r by using a coordinate conversion function (conversion parameter) estimated in step S3.

Furthermore, in step S5, the display 8 overlays the probe attachment position r' calculated in step S4 on a two-dimensional video image to display. In this regard, the above procedure of steps S1 to S5 illustrated in FIG. 3 is executed in real time.

Hereinafter, the measuring instrument attachment assist method illustrated in FIG. 3 will be described in detail.

First, a method for detecting the feature point indicated in step S2 in FIG. 3 will be described in detail based on an example of a case where feature points (reference markers) of the shape are automatically detected from the two-dimensional image of the subject head with reference to FIGS. 4 and 5.

Figure 4:
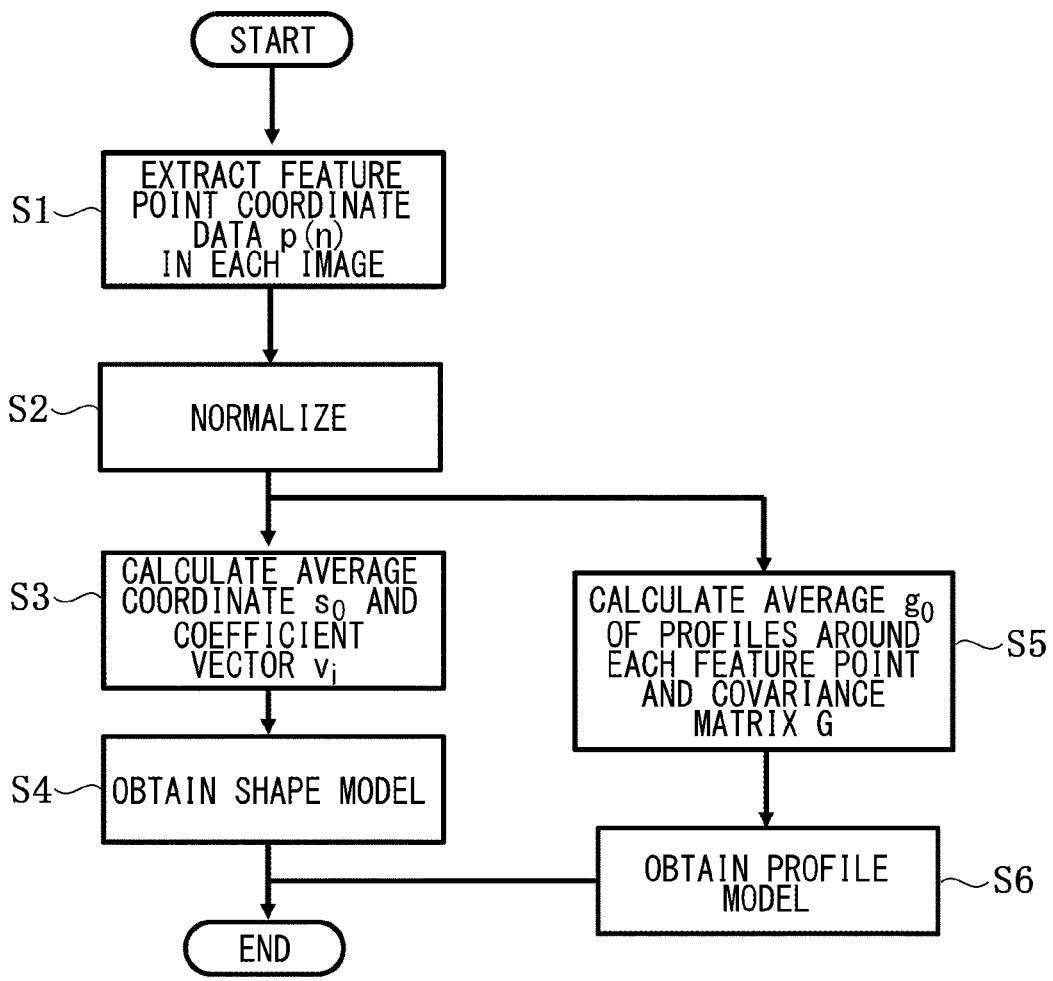
FIG. 4 is a flowchart illustrating a creating method of a model image illustrated in FIG. 2.

FIG. 4 is a flowchart illustrating a method for creating the prediction model indicated in step S11 in FIG. 3. The method for creating the prediction model will be specifically described below with reference to FIG. 4.

Coordinates of feature points such as a root of the nose, an auricle and a corner of the eye on face images of multiple people are designated to create teacher data. Furthermore, the created teacher data is used to execute machine learning, and construct a prediction model expressed by a numerical formula.

More specifically, coordinates p(n) (referred to as "feature point coordinate data" below) of m anatomical feature points are extracted in each of n digital images (face images) showing human faces in step S1, and are normalized in step S2.

In addition, normalized feature point coordinate data $s_n$ is created by arranging coordinates $(x_i, y_i)$ on a two-dimensional space of feature points such as a right eye center, a left eye center, a lip right end and a lip left end as expressed in, for example, following equation (1) in predetermined order, and such a format is regarded as common between all items of feature point coordinate data.

$$s_n = [x_1, y_1, \ldots, x_m, y_m]^T \quad (1)$$

Next, in step S3, an average coordinate $s_0$ which is an average of all items of feature point coordinate data, and a coefficient (displacement) vector $v_i$ are calculated. In this regard, the displacement vector $v_i$ is calculated by principal component analysis performed on a data matrix X expressed in, for example, following equation (2). In addition, i represents the number of displacement vectors.

$$X = [s_1, s_2, \ldots, s_n] \quad (2)$$

Next, in step S4, a shape model including all items of feature point coordinate data s expressed in following equation (3) is obtained by using a displacement amount $a_i$.

$$s = s_0 + \Sigma a_i v_i = Va \quad (3)$$

In above equation (3), a vector V is a vector generated from the displacement vector $v_i$, and a matrix a is a matrix generated from the displacement amount $a_i$.

On the other hand, in step S5, a luminance profile $g_{m,n}$ of each feature point in surrounding pixels is obtained. This luminance profile is, for example, a one-dimensional vector which can be obtained by obtaining luminance values of (3×3) pixels around a certain feature point of a face image, standardizing the luminance values such that a maximum value of these luminance values is 1 and a minimum value is 0, and arranging the standardized luminance values of the (3×3) pixels in determined order of, for example, (x−1, y−1), (x, y−1), (x+1, y−1), (x−1, y), (x, y), (x+1, y), (x−1, y+1), (x, y+1) and (x+1, y+1).

Next, an average $g_0$ of luminance profiles around each feature point, and a covariance matrix G are calculated. In this regard, the covariance matrix G indicates a variation, and is a variance-covariance matrix created by, for example, a data matrix $(g_{m,0}, g_{m,1}, \ldots, g_{m,n})$.

Thus, in step S6, a profile model including the m averages $g_{0,m}$ and a covariance matrix $G_m$ calculated by the above method is obtained.

Figure 5:
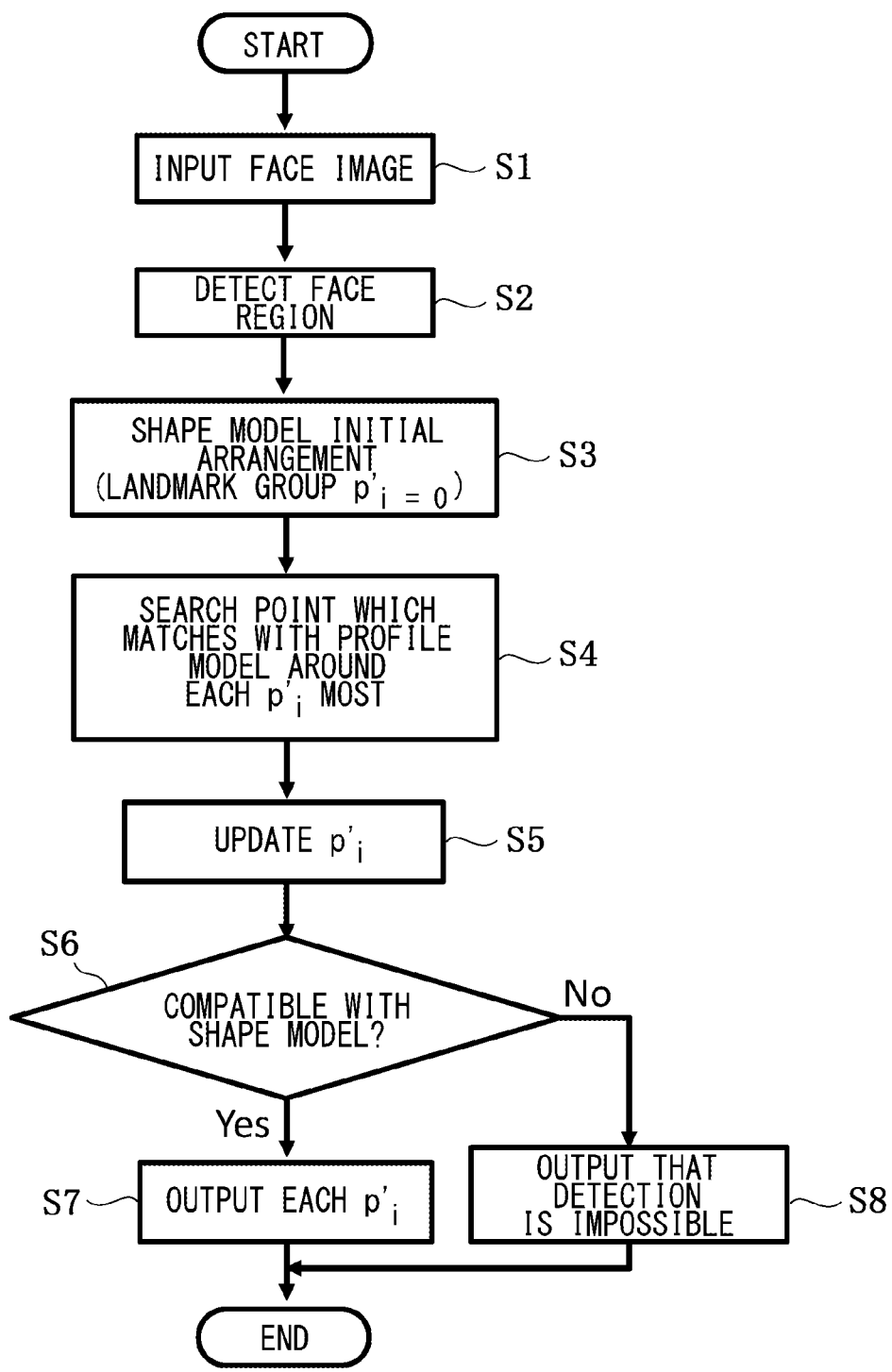
FIG. 5 is a flowchart illustrating a method for automatically detecting feature points illustrated in FIG. 2.

FIG. 5 is a flowchart illustrating a method for automatically detecting coordinates of feature points (reference markers) in step S2 in FIG. 3. A method where the coordinate detector 4 automatically detects the reference markers will be specifically described below with reference to FIG. 5.

In step S1, the coordinate detector 4 receives an input of a face image via the input/output terminal 2 and the bus 3. In this regard, the face image may be stored in advance in the storage which is not illustrated in FIG. 1 and is connected to the bus 3, and this face image may be inputted to the coordinate detector 4 via the bus 3.

Next, in step S2, the coordinate detector 4 detects a face region in each inputted image. In this regard, a face region means a region including an entire region defined as a rectangular shape. There is a method for using a Harr-like feature to detect this face region Φ.

Next, in step S3, the coordinate detector 4 initially arranges the shape model in the detected face region detected in step S2. According to this initial arrangement, when, for example, the Harr-like feature is used to detect the face region, a direction of the face can be specified, and therefore the shape model is arranged such that a gravitational center of the average coordinate $s_0$ in the shape model matches with the center of the face region Φ. In addition, this initial arrangement determines an initial coordinate $p'_{i=0}$ of an anatomical landmark group corresponding to the above feature points (reference markers).

Next, in step S4, the coordinate detector 4 provides a search region near each of the coordinates $p'_i$ of the m feature points, and searches for a pixel (point) having a profile which matches with the profile model the most in each search region. In addition, the search region is, for example, a rectangular shape of (5×5).

In this regard, a scale $f_p$ of similarity of the profile is expressed as in the following equation by using a luminance profile $g'_{m,i}$ of each point in the search region.

$$f_p = (g_{m,0} - g'_{m,i})^T G^{-1} (g_{m,0} - g'_{m,i}) \quad (4)$$

Furthermore, in step S5, the coordinate detector 4 updates the coordinates $p'_i$ of the feature points to such coordinates that the scale $f_p$ in each search region is minimum. After the coordinates of all feature points are updated in this way, the coordinate detector 4 inspects compatibility of the image of the face region detected in step S2 and the shape model in step S6.

In this case, when the scale $f_s$ calculated by following equation (5) is smaller than a certain value, the flow moves to step S7, and the coordinate detector 4 outputs the coordinates $p'_i$ as feature points. When the scale $f_s$ is not smaller than the certain value, the flow moves to step S8, and the coordinate detector 4 outputs data indicating that the coordinates $p'_i$ cannot be estimated as the feature points, and detection is impossible.

$$f_s = \|p_i' - s\|^2 \quad (5)$$

A method where the conversion parameter calculator 5 estimates a coordinate conversion function f by calculating the projection conversion parameter in step S3 illustrated in FIG. 3 will be specifically described below. In addition, a case where the feature points detected in step S2 illustrated in FIG. 3 are two-dimensional reference markers, and a model image is a three-dimensional anatomical image of the subject will be described as one example.

First, the three-dimensional anatomical image of the head of the subject is obtained by magnetic resonance imaging (MRI). This image only needs to be able to allow a surface of the brain or the scalp of the subject to be easily identified, and is, for example, a T1 weighted image. Furthermore, the user sets a virtual space coordinate system based on luminance information of the MRI by using the designating unit 7, and designates coordinates $p_i (X_i, Y_i, Z_i)$ of a plurality of anatomical reference points on the scalp surface.

In addition, this designated reference points correspond to feature points recorded on the two-dimensional space described with reference to FIG. 4 as described above, and recorded in predetermined order.

An optional point x on a three-dimensional head anatomical image can be projected on a coordinate x″ on the two-dimensional image recorded by a video camera according to following equation (6).

$$sx'' = A[R|t]x \quad (6)$$

In this regard, s represents a magnification factor, A represents a matrix of (2×3) including a center coordinate of a projection plane and a focal distance, and s and A are known parameters which are given as image capturing conditions of the two-dimensional image. On the other hand, R and t represent a rotation matrix and a displacement vector, respectively, and have arbitrariness as projection conversion parameters. However, by cross-checking in this two-dimensional image such that a projection p″$_i$ of a feature point group of the three-dimensional virtual space matches with the feature point group p′$_i$ detected in the same image space the most, it is possible to uniquely determine the rotation matrix R and the displacement vector t.

By using the rotation matrix R and the displacement vector t determined in this way, it is possible to project the any point x on the virtual space on the point x″ on the two-dimensional coordinate of an actual space by using equation (6). In addition, for example, linear programming can be used to determine the rotation matrix R and the displacement vector t.

Next, a method where the coordinate converter 6 converts the position coordinate of the attached measuring instrument by equation (6) by using the calculated, projection conversion parameter in step S4 illustrated in FIG. 3, and the display 8 displays the converted position coordinate in step S5 illustrated in FIG. 3 will be specifically described. In this regard, a case where an attachment position of the probe is two-dimensionally projected on the moving video image will be described as one example.

The user designates a center coordinate $r_b$ of a brain region which is a measurement target by using the designating unit 7 based on the luminance information from the three-dimensional head anatomical image. The coordinate converter 6 calculates a position to which the probe needs to be attached, i.e., the coordinate r′ on the two-dimensional video image by using following equation (7) based on, for example, the coordinate r of the scalp position which is directly above the center coordinate $r_b$.

$$r'=A[R|t]r/s \qquad (7)$$

Furthermore, the display 8 overlays on the two-dimensional video image the position of the coordinate r′ calculated by using equation (7) to display.

In addition, the brain surface has protrusions and recesses, and therefore a normal line on the center coordinate $r_b$ does not necessarily pass simply a point directly above the center coordinate $r_b$. Hence, such a coordinate $r_s$ at a point on the scalp that a Euclidean distance from the center coordinate $r_b$ is the shortest is calculated. Furthermore, the coordinate $r_s$ calculated by this method is the coordinate r at the scalp position, and the probe needs to be attached such that this point is a center of an irradiation point and a detection point of the probe.

By executing a series of above processing with respect to moving images in the real time, it is possible to check the position to which the probe needs to be attached on the two-dimensional moving image in real time even when the two-dimensional moving image of the subject head is monitored and when the head of the subject or a videographer is moving.

Figure 6:
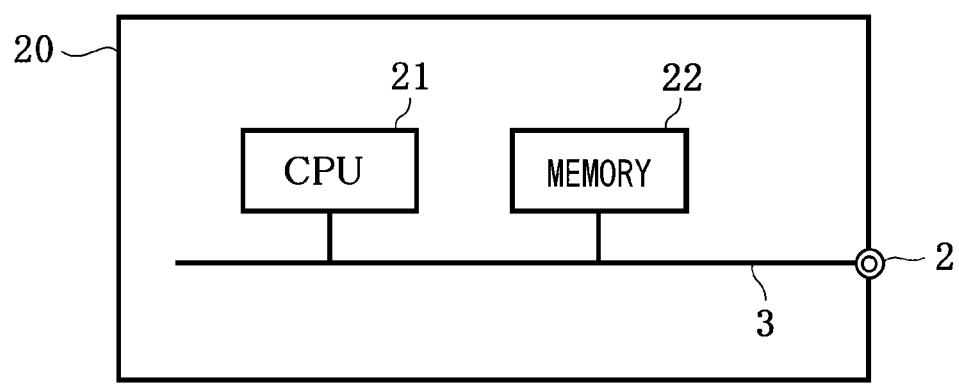
FIG. 6 is a diagram illustrating another configuration example of the measuring instrument attachment assist device according to the first embodiment of the present invention.

In addition, the above measuring instrument attachment assist method can be expressed as a program which enables a computer to execute the procedure illustrated in FIGS. 2 to 5, and can be also realized by storing this program in a memory 22 of a measuring instrument attachment assist device 20 illustrated in FIG. 6 and causing a CPU 21 to execute the program.

Figure 7:
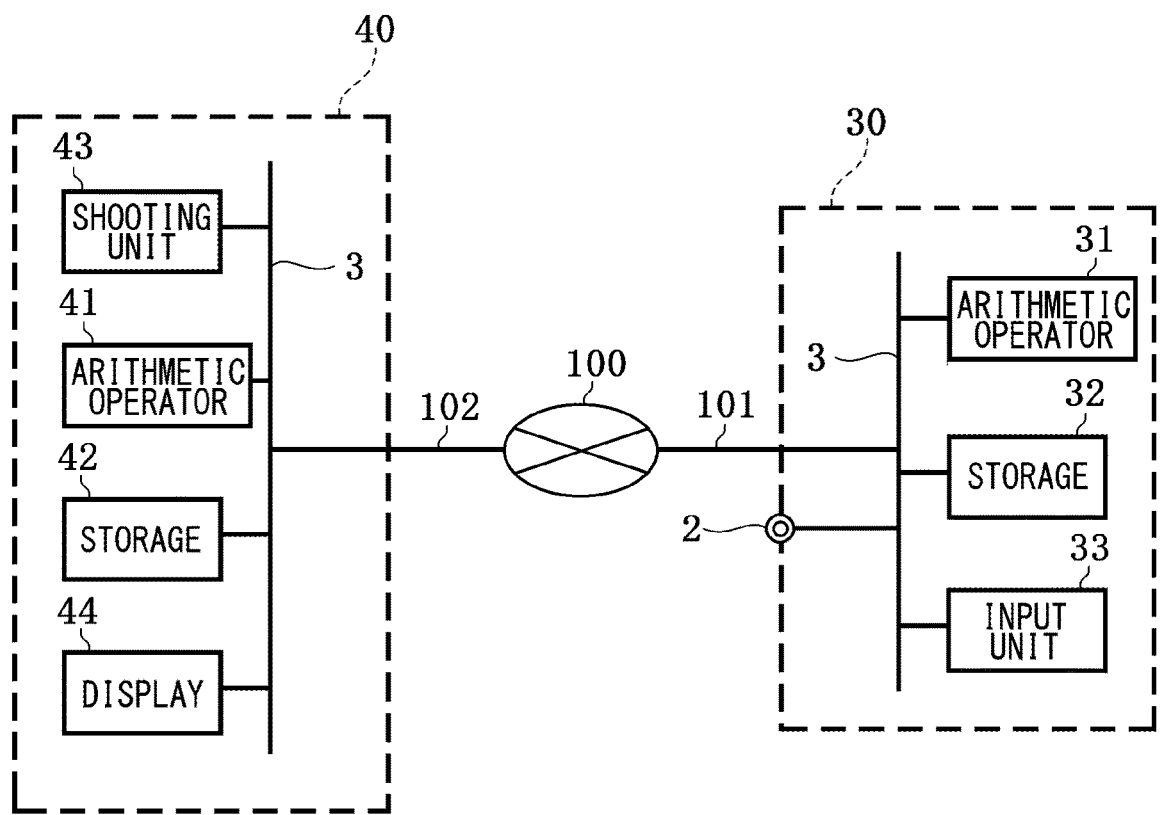
FIG. 7 is a block diagram illustrating still another configuration example of the measuring instrument attachment assist device according to the first embodiment of the present invention.

Furthermore, the above measuring instrument attachment assist method can be realized by a measuring instrument attachment assist device illustrated in FIG. 7. In this regard, the measuring instrument attachment assist device illustrated in FIG. 7 includes a Personal Computer (PC) 30 and a portable terminal 40 which are connected to a network 100 via Internet lines 101 and 102.

In this regard, the PC 30 includes the input/output terminal 2 and the bus 3 which is connected to the input/output terminal 2 and the Internet line 101, and an arithmetic operator 31, a storage 32 and an input unit 33 which are respectively connected to the bus 3. Furthermore, the portable terminal 40 includes the bus 3 which is connected to the Internet line 102, and an arithmetic operator 41, a storage 42, a shooting unit 43 and a display 44 which are respectively connected to the bus 3. Hereinafter, an operation of the measuring instrument attachment assist device employing this configuration will be described.

First, the PC 30 stores head anatomical structure data obtained by MRI in advance in the storage 32 via the input/output terminal 2 or the Internet line 101, and the bus 3. Furthermore, similarly, the PC 30 stores a face image and feature points of the face image from the face image DB to the storage 32 via the input/output terminal 2 or the Internet line 101, and the bus 3. Furthermore, the arithmetic operator 31 creates a prediction model by using an image stored in the storage 32.

Next, when the user designates a plurality of feature points $p_i$ on a skin surface of the head anatomical structure data by using the input unit 33, and further designates measurement target brain tissues, the arithmetic operator 31 calculates the probe attachment position r on the skin surface directly above the brain tissues. Furthermore, the prediction model created by the arithmetic operator 31 and the calculated probe attachment position r are transferred to the storage 42 of the portable terminal 40 via the Internet lines 101 and 102, the network 100, and the bus 3.

In the portable terminal 40, the arithmetic operator 41 calculates the feature points p′$_i$ on a video frame corresponding to the feature points $p_i$ set in a virtual space based on one frame which captures the face of the subject in a video moving image of the face obtained by shooting by the shooting unit 43, and the prediction model stored in the storage 42.

Furthermore, the arithmetic operator 41 finds a mapping function f of converting the feature points $p_i$ into the feature points p′$_i$, and converts the probe attachment position r in the same space as the feature points $p_i$ into the position r′ of a video frame coordinate system. Furthermore, the display 44 displays the position r′ on a video frame.

Thus, the portable terminal 40 executes the above processing in real time, so that the user can check the probe attachment position on the scalp in video moving images shot from various angles by the portable terminal 40 and consequently can accurately learn the precise three-dimensional probe attachment position of the subject head.

Figure 8:
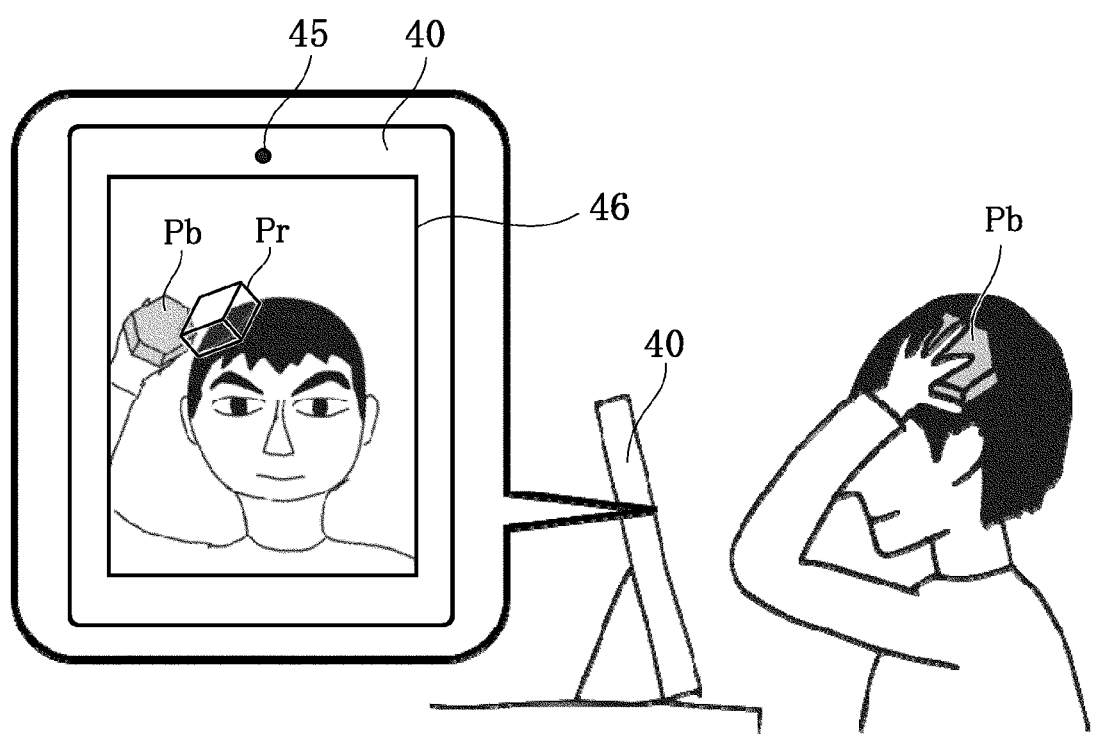
FIG. 8 is a view illustrating a specific example of a portable terminal 40 illustrated in FIG. 7.

In addition, the portable terminal 40 illustrated in FIG. 7 is realized by a smartphone and, in addition, a tablet computer illustrated in FIG. 8 and a head mount display which can perform parallel processing of capturing and displaying of moving images, and arithmetic operation processing and can be carried by the user.

In this regard, the display 44 included in the portable terminal 40 is configured as a display 46 as illustrated in, for example, FIG. 8. However, it is considered to configure the shooting unit 43 as cameras provided on a back side and a front side of the display.

In this case, one of the cameras provided on the back side and the front side may be optionally selected by the user. This is because the one portable terminal 40 can realize two patterns of usage that, when the camera on the back side is selected, the operator captures an image of a head of a subject while holding the portable terminal 40, and, when a camera 45 on the front side is selected, the subject captures an image of a head of the subject as illustrated in FIG. 8.

Furthermore, when the camera on the front side is selected, the arithmetic operator 41 included in the portable terminal 40 reverses the image captured by the camera with respect to a vertical axis and causes the display to display the image, so that the subject can see the head of the subject like a mirror as illustrated in FIG. 8, and consequently can intuitively learn a position Pr at which a probe Pb needs to be attached to the head.

On the other hand, when the camera on the back side is selected, for example, the operator can adjust the position Pr at which the probe Pb needs to be attached by a method for holding the portable terminal 40 by the one hand and capturing images of the head of the subject from various angles while viewing the display 46, and putting the probe Pb at a predetermined position by the other hand.

As described above, the measuring instrument attachment assist device and the measuring instrument attachment assist method according to the embodiment of the present invention can easily assist precise attachment of the probe to a head surface directly above a desired brain region without using a special marker or a large device which is conventionally necessary. Furthermore, it is possible to precisely attach the probe, and consequently it is not necessary to attach multiple probes.

Second Embodiment

Figure 9:
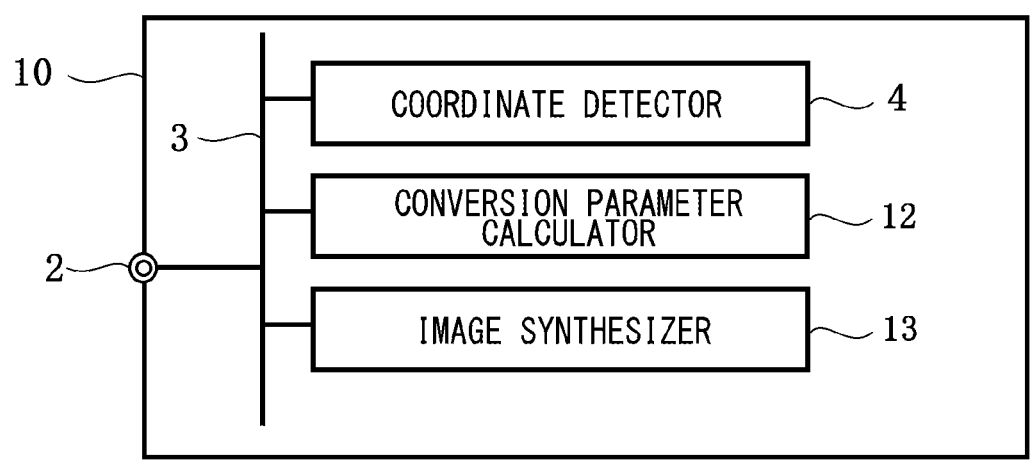
FIG. 9 is a block diagram illustrating a configuration example of a measuring instrument attachment assist device according to a second embodiment of the present invention.

FIG. 9 is a block diagram illustrating a configuration example of the measuring instrument attachment assist device according to the second embodiment of the present invention. As illustrated in FIG. 9, a measuring instrument attachment assist device 10 includes an input/output terminal 2, a bus 3 which is connected to the input/output terminal 2, and a coordinate detector 4, a conversion parameter calculator 12 and an image synthesizer 13 which are respectively connected to the bus 3.

In addition, the measuring instrument attachment assist device 10 performs the same operation as that of the measuring instrument attachment assist device according to the first embodiment. Therefore, description of common points will be omitted, and differences will be described below.

The conversion parameter calculator 12 calculates a projection conversion parameter for converting coordinates of feature points in a brain surface shape image of a subject obtained by MRI in advance into coordinates obtained by detection by the coordinate detector 4 by the same method as the above measuring instrument attachment assist method executed by a conversion parameter calculator 5 illustrated in FIG. 1.

Furthermore, the image synthesizer 13 synthesizes the brain surface shape image and the capturing image by finding corresponding points between the captured image and the brain surface shape image by using the projection conversion parameter calculated by the conversion parameter calculator 12, and overlaying the corresponding points.

In addition, the brain surface shape image and the captured image are obtained from an outside of the measuring instrument attachment assist device 10 via the input/output terminal 2. In this regard, as for the captured image, an imager and a storage may be further provided inside the measuring instrument attachment assist device 10, and images captured by the imager may be stored in the storage.

The measuring instrument attachment assist device 10 according to the above second embodiment of the present invention can overlay and display the brain surface shape image on a head image of a user captured in real time by performing real-time processing similar to the measuring instrument attachment assist device according to the first embodiment, so that the user can attach a probe while checking a brain region without designating a probe attachment position in advance.

In addition, for example, information such as a classification or a label of each brain region, a functional magnetic resonance image, a distribution image of a brain function activity signal based on an electroencephalograph, and a probe position recorded during previous measurement.

Furthermore, a probe shape may be registered in advance in a database, and this probe shape may be displayed on a subject head image in a real space instead of displaying a probe position.

DESCRIPTION OF THE REFERENCE NUMERALS

1, 10, 20 measuring instrument attachment assist device, 4 coordinate detector, 5, 12 conversion parameter calculator, 6 coordinate converter, 7 designating unit, 8, 44 display, 13 image synthesizer, 21 central processing unit (CPU), 22 memory, 30 personal computer (PC), 31, 41 arithmetic operator, 32, 42 storage, 33 input unit, 40 portable terminal, 45 camera, 46 display

The invention claimed is:

1. A measuring instrument attachment assist device comprising:
    a coordinate detector structured to detect a coordinate of a predetermined feature point from an image obtained by capturing an image of a subject;
    a conversion parameter calculator structured to calculate a projection conversion parameter for converting a coordinate of the feature point in a three-dimensional head anatomical image into the coordinate obtained by the detection;
    a designating unit structured to designate a position of a measuring instrument attached to the subject in the three-dimensional head anatomical image;
    a coordinate converter structured to convert a coordinate of the position by using the projection conversion parameter, the position being designated by using the designating unit; and
    a display structured to display the coordinate obtained by the conversion by the coordinate converter, on the image obtained by the capturing,
    wherein the designating unit designates a center coordinate of a brain region which is a measurement target based on luminance information from the three-dimensional head anatomical image,
    wherein the coordinate converter calculates a coordinate on the image obtained by the capturing, which correspond to a position at which the measuring instrument is attached to the subject, by a conversion using the projection conversion parameter based on a coordinate of a scalp position which is directly above the designated center coordinate of the brain region, and
    wherein a coordinate at a point on the scalp that a Euclidean distance from the center coordinate is the shortest is calculated, and the coordinate is defined as a center of an irradiation point and a detection point of the measuring instrument.

2. The measuring instrument attachment assist device according to claim 1, wherein
the image obtained by the capturing is a moving image,
the coordinate detector detects the coordinate of the predetermined feature point in real time,
the conversion parameter calculator calculates the projection conversion parameter in real time,
the coordinate converter converts the coordinate of the position by using the projection conversion parameter calculated in real time, the position being designated by using the designating unit, and
the display displays on the moving image in real time the coordinate obtained in real time by the conversion by the coordinate converter.

3. The measuring instrument attachment assist device according to claim 2, further comprising an imager structured to capture the image of the subject, wherein
the display reverses the moving image captured by the imager horizontally with respect to a vertical axis to display.

4. The measuring instrument attachment assist device according to claim 1, wherein
the image obtained by the capturing is a two-dimensional image, and
the model image is a three-dimensional image.

5. A measuring instrument attachment assist method comprising:
a first step of detecting a coordinate of a predetermined feature point from an image obtained by capturing an image of a subject;
a second step of calculating a projection conversion parameter for converting a coordinate of the feature point in a three-dimensional head anatomical image into the coordinate obtained by the detection; and
a third step of converting a position coordinate by using the projection conversion parameter, and displaying the converted coordinate in the image obtained by the capturing, the position coordinate being a position coordinate which is designated in the three-dimensional head anatomical image, and at which a measuring instrument is attached to the subject,
wherein a center coordinate of a brain region which is a measurement target is designated based on luminance information from the three-dimensional head anatomical image,
wherein the third step calculates a coordinate on the image obtained by the capturing, which correspond to a position at which the measuring instrument is attached to the subject, by a conversion using the projection conversion parameter based on a coordinate of a scalp position which is directly above the designated center coordinate of the brain region, and
wherein a coordinate at a point on the scalp that a Euclidean distance from the center coordinate is the shortest is calculated, and the coordinate is defined as a center of an irradiation point and a detection point of the measuring instrument.

6. The measuring instrument attachment assist method according to claim 5, wherein
the image obtained by the capturing is a moving image,
in the first step, the coordinate of the predetermined feature point is detected in real time,
in the second step, the projection conversion parameter is calculated in real time, and
in the third step, the conversion is performed by using the projection conversion parameter in real time, and the converted coordinate is displayed in the moving image in real time.

7. The measuring instrument attachment assist method according to claim 6, wherein, in the third step, the moving image obtained by the capturing is horizontally reversed with respect to a vertical axis to display.

8. The measuring instrument attachment assist method according to claim 5, wherein
the image obtained by the capturing is a two-dimensional image, and
the model image is a three-dimensional image.

* * * * *